(12) United States Patent
Kitten

(10) Patent No.: US 10,548,945 B2
(45) Date of Patent: Feb. 4, 2020

(54) TOPICAL COMPOSITIONS COMPRISING OB-FOLD VARIANTS

(71) Applicant: AFFILOGIC, Nantes (FR)

(72) Inventor: Olivier Kitten, Nantes (FR)

(73) Assignee: AFFILOGIC, Nantes (FR)

( * ) Notice: Subject to any disclaimer, the term of this patent is extended or adjusted under 35 U.S.C. 154(b) by 0 days.

(21) Appl. No.: 14/786,287

(22) PCT Filed: Apr. 22, 2014

(86) PCT No.: PCT/EP2014/058139
§ 371 (c)(1),
(2) Date: Oct. 22, 2015

(87) PCT Pub. No.: WO2014/173899
PCT Pub. Date: Oct. 30, 2014

(65) Prior Publication Data
US 2016/0143990 A1 May 26, 2016

(30) Foreign Application Priority Data

Apr. 22, 2013 (FR) ..................................... 13 53662

(51) Int. Cl.
| | | |
|---|---|---|
| A61K 38/16 | (2006.01) | |
| A61K 9/00 | (2006.01) | |
| A61K 9/08 | (2006.01) | |
| A61K 45/06 | (2006.01) | |

(52) U.S. Cl.
CPC ............ *A61K 38/16* (2013.01); *A61K 9/0014* (2013.01); *A61K 9/0048* (2013.01); *A61K 9/08* (2013.01); *A61K 45/06* (2013.01)

(58) Field of Classification Search
CPC ............................ A61K 9/0014; A61K 9/0048
See application file for complete search history.

(56) References Cited

U.S. PATENT DOCUMENTS

| 2010/0145008 A1* | 6/2010 | Pecorari | ............... | C07K 14/195 |
| | | | | 530/324 |
| 2011/0207668 A1* | 8/2011 | Binz | .................. | C07K 14/4703 |
| | | | | 514/13.3 |

FOREIGN PATENT DOCUMENTS

| WO | WO-2008/068637 A2 | 6/2008 |
| WO | WO-2012/150314 A1 | 11/2012 |

OTHER PUBLICATIONS

Murzin "OB(oligonucleotide/oligosaccharide binding)-fold: common structural and functional solution for non-homologous sequences" The EMBO Journal, 1993, vol. 12 No. 3 pp. 861-867.*
Arcus "OB-fold domains: a snapshot of the evolution of sequence, structure and function," Current Opinion in Structural Biology 2002, 12:794-801.*
Kalluri et al. "Transdermal Delivery of Proteins," AAPS PharmSciTech, 2011, vol. 12, pp. 431-441.*
Huang et al. "Synthetic Skin-Permeable Proteins Enabling Needleless Immunization" Angew Chem Int Ed Engl., 2010, vol. 49, 2724-2727.*
Arcus, Vickery: "OB-fold domains: a snapshot of the evolution of sequence, structure and function", Current Opinion in Structural Biology, Elsevier Ltd, GB, vol. 12, No. 6, Dec. 1, 2002, pp. 794-801.
International Search Report, PCT/EP2014/058139.
Cited Document 1, document cited in a corresponding Japanese Office Action dated Dec. 27, 2017 and Partial English Translation.

* cited by examiner

*Primary Examiner* — Christina Bradley
(74) *Attorney, Agent, or Firm* — Polsinelli PC

(57) ABSTRACT

The invention relates to a topical composition containing a variant of an OB-fold protein, and also to the process for preparing the same.

10 Claims, 1 Drawing Sheet
Specification includes a Sequence Listing.

| Date | | | J4 | | | J5 | | | J6 | | | J7 | | |
|---|---|---|---|---|---|---|---|---|---|---|---|---|---|---|
| Ear | | Right | Left | RE-LE / LE | Right | Left | RE-LE / LE | Right | Left | RE-LE / LE | Right | Left | RE-LE / LE |
| Nanofitine E8 | Total score Mean Deviation | 16,00 4,00 2,12 | 29,00 7,25 0,5 | -45% | 19,00 4,75 1,71 | 28,00 7,00 0,82 | -32% | 14,50 3,63 1,11 | 22,00 5,50 0,58 | -34% | 15,50 3,88 0,85 | 28,00 7,00 0,00 | -45% |
| Nanofitine G2 | Total score Mean Deviation | 14,50 3,63 0,75 | 31,00 7,75 0,50 | -53% | 11,00 2,75 0,96 | 30,00 7,50 0,58 | -63% | 10,00 2,50 0,58 | 32,00 8,00 1,41 | -69% | 9,00 2,25 1,32 | 29,00 7,25 0,50 | -69% |
| Nanofitine N2 | Total score Mean Deviation | 13,50 3,38 0,48 | 29,00 7,25 0,96 | -53% | 10,00 2,50 1,00 | 29,00 7,25 0,96 | -66% | 9,00 2,25 0,50 | 28,00 7,00 0,82 | -68% | 9,00 2,25 0,50 | 30,00 7,50 1,00 | -70% |
| Nanofitine N9 | Total score Mean Deviation | 14,00 3,50 2,00 | 23,00 5,75 2,87 | -39% | 8,00 2,00 1,00 | 21,00 5,25 0,85 | -62% | 10,00 2,50 1,00 | 24,50 6,13 2,93 | -59% | 5,00 1,25 0,00 | 24,50 6,13 2,78 | -80% |
| Clobétazole | Total score Mean Deviation | 11,00 2,75 1,50 | 22,00 5,50 1,00 | -50% | 4,00 1,00 0,71 | 11,00 2,75 0,96 | -64% | 1,50 0,38 0,48 | 10,00 2,50 0,58 | -85% | 1,00 0,25 0,50 | 9,00 2,25 0,96 | -89% |
| Véhicule PBS/20% EtOH | Total score Mean Deviation | 23,50 5,88 1,03 | 31,00 7,75 0,96 | -24% | 26,50 6,63 1,31 | 32,00 8,00 0,00 | -17% | 26,00 6,50 0,71 | 31,00 7,75 0,96 | -16% | 25,50 6,38 0,63 | 27,50 6,88 0,25 | -7% |

TOPICAL COMPOSITIONS COMPRISING OB-FOLD VARIANTS

RELATED APPLICATIONS

This application is a national stage application (under 35 U.S.C. § 371) of PCT/EP2014/058139, filed Apr. 22, 2014, which claims benefit of French application FR 13/53662, filed Apr. 22, 2013.

SUBMISSION OF SEQUENCE LISTING

The Sequence Listing associated with this application is filed in electronic format via EFS-Web and hereby incorporated by reference into the specification in its entirety. The name of the text file containing the Sequence Listing is 15351_32_Sub_Seq_List. The size of the text file is 7 KB, and the text file was created on Feb. 1, 2016.

The invention relates to the field of the preparation of topical compositions for cosmetic or therapeutic use, containing active ingredients which bind to targets of interest.

There are a certain number of dermatological diseases, such as eczemas, psoriasis, lichen planus and autoimmune bullos dermatoses, or skin cancers (melanoma). In order to treat these diseases, it is desirable to be able to have topical compositions, that is to say compositions which are applied directly to the skin lesions (or scalp lesions) and which act locally at the site where they are applied.

Moreover, such topical compositions are desirable for the treatment of ocular diseases, whether they are associated with metabolic disregulation (in particular due to age) or to ocular infections (severe conjunctivitis, keratitis and corneal ulcers).

Whatever the disease, there is generally a target of therapeutic interest on which the medicaments are active. This may be a cell receptor, or a surface protein of a microorganism. Generally, it appears to be desirable to have compositions enabling the application of active ingredients which act on the targets of therapeutic interest directly on the site of action, avoiding as much as possible any passage via the systemic route. However, antibodies do not easily penetrate the skin barrier or the corneal barrier.

Patent application WO 2007/139397 describes the use of libraries of OB-fold proteins in which the OB domain is modified by introducing mutations into this domain for binding the protein to its natural ligand.

Patent application WO 2008/068637 describes the use of a library based on the Sac7d protein for obtaining ligands which have an affinity for targets of interest. The method described in WO 2008/068637 comprises the generation of combinatorial libraries containing a plurality of DNA molecules all having the same sequence, except for the presence of certain random mutations leading to the production of variants of a wild-type protein, exhibiting mutations at certain amino acids of the binding site of this wild-type OB-fold protein. In particular, in the context of WO 2008/068637, the wild-type OB-fold protein is a Sac7d protein, into which mutations are introduced in order to generate a variability, in particular at amino acids chosen from K7, Y8, K9, K21, K22, W24, V26, M29, S31, T33, T40, R42, A44 and S46, or on other amino acids, such as V26, G27, K28, M29, S31, R42, A44, S46, E47 and K48. These amino acids are based on the Sac7d sequence as represented by SEQ ID No. 1.

Patent application WO 2012/150314 presents the portability of mutations from one protein of the Sac7d family to another protein of the same family. This portability amounts to creating a mutant of another protein of the Sac7d family from a mutant of one protein of said family, that it has been possible to obtain in particular by carrying out the process of WO 2008/068637.

The Sac7d family is defined as relating to the Sac7d family corresponds to a family of 7 kDa DNA-binding proteins isolated from extremophilic bacteria. These proteins and this family are in particular described in WO 2008/068637. Thus, within the context of the present invention, a protein belongs to the Sac7d family when it has a sequence corresponding to the sequence SEQ ID No. 8. This family comprises in particular the Sac7d or Sac7e proteins obtained from *Sulfolobus acidocaldarius*, the Sso7d protein obtained from *Sulfolobus solfataricus*, the DBP 7 protein obtained from *Sulfolobus tokodaii*, the Ssh7b protein obtained from *Sulfolobus shibatae*, the Ssh7a protein obtained from *Sulfolobus shibatae*, and the p7ss protein obtained from *Sulfolobus solfataricus*.

The OB-fold proteins are known in the art. They are in particular described in the documents described above, and also in Arcus (Curr Opin Struct Biol. 2002 December; 12(6):794-801). OB-fold is in the form of a cylinder having five beta (β) sheets. Most OB-fold proteins use the same binding interface for their natural ligand, which may be an oligosaccharide, an oligonucleotide, a protein, a metal ion or a catalytic substrate. This binding interface comprises mainly the residues located in the beta sheets. Certain residues located in the loops may also be involved in the binding of an OB-fold protein with its natural ligand. Thus, applications WO 2007/139397 and WO 2008/068637 and the Arcus document (2002, op. cit.) describe the OB-fold-protein domains for binding with their natural ligand. Thus, document WO 2008/068637 describes precisely how to identify the binding domain of an OB-fold protein.

By superimposing several sequences and 3D structures of proteins having OB-fold domains, using the websites WU-Blast2 (http://www.ebi.ac.uk/blast2/index.html) (Lopez et al., 2003, Nucleic Acids Res 31, 3795-3798), T-COFFEE (http://www.ch.embnet.org/software/TCoffee.html) (Notredame et al., 2000, J Mol Biol 302, 205-217) and DALI lite (http://www.ebi.ac.uk/DaliLite/) (Holm and Park, 2000, Bioinformatics 16, 566-567), it is possible to identify the positions of the binding domains and in particular the amino acids which can be modified. Taking the sequence of Sac7d (SEQ ID No. 1) as reference, these are the residues V2, K3, K5, K7, Y8, K9, G10, E14, T17, K21, K22, W24, V26, G27, K28, M29, S31, T33, D36, N37, G38, K39, T40, R42, A44, S46, E47, K48, D49, A50 and P51. Still with this Sac7d sequence as reference, the residues which can be deleted are: A59, R60, A61 and E64.

The binding domains of other OB-fold proteins can be identified as described in WO 2008/068637. This application indicates that it is possible to perform a superimposition of 3D structures of OB-fold proteins or domains (ten domains were used in this application, including Sac7d), using the DALI website (http://www.ebi.ac.uk/dali/interactive.html) (Holm and Sander, 1998, Nucleic Acids Res 26, 316-319). Thus, it is easy to identify, for any OB-fold protein (or any OB-fold domain), the amino acids involved in the binding site and corresponding to the Sac7d amino acids mentioned above.

The teaching of WO 2008/068637 also indicates that amino acids can optionally be inserted into the loops of the OB-fold proteins, in particular the proteins of the Sac7d family; in particular, insertions of 1 to 15 amino acid residues can be made in loop 3 (as defined in FIGS. 1b and 2 of WO 2008/068637), for example in the region of residues 25 to 30 of Sac7d, preferably between residues 27 and 28, insertions of 1 to 15 amino acid residues can be made in loop 4 (as defined in FIGS. 1b and 2 of WO 2008/068637), for example in the region of residues 35-40 of Sac7d, preferably between residues 37 and 38, and insertions of 1 to 20 residues can be made in loop 1 (as defined in FIGS. 1b and 2 of WO 2008/068637), for example in the region of residues 7 to 12 of Sac7d, preferably between residues 9 and 10.

By extension, in the context of the present application, the term "OB-fold protein" also comprises the domains which have an OB-fold that can be isolated from more complex proteins. These OB-fold domains are in particular described in greater detail in applications WO 2007/139397 and WO 2008/068637.

The advantage of the method described in WO 2008/068637 is that it makes it possible to obtain variants of OB-fold proteins by screening combinatorial libraries containing or expressing a plurality of variants in which a certain number of amino acids have been "randomized", i.e. replaced with a random amino acid.

The screening of these libraries makes it possible to identify variants of these proteins which bind specifically, generally with a strong affinity (application WO 2008/068637 indeed describes affinities of the order of one nanomolar), with a target of interest, other than the natural ligand of the wild-type protein from which the combinatorial library was generated.

The inventors have shown that the OB-fold proteins are capable of crossing the ocular barrier or the skin barrier and can therefore be used in topical compositions. Use is preferably made of a variant of an OB-fold protein, which binds to a target of interest, said target of interest being involved in a pathological condition, in particular an ophthalmological or dermatological condition.

The present invention thus relates to a topical composition comprising an OB-fold protein or a variant of a wild-type OB-fold protein, said variant having between 5 and 32 mutated residues in the interface of binding of said wild-type OB-fold protein to its natural ligand. In one particular embodiment, said variant binds specifically to a target of interest other than said natural ligand. This variant was therefore generally identified by implementing a method as described in WO 2008/068637 or WO 2007/139397. In fact, the implementation of the methods described in these two patent applications generally makes it possible to identify variants of any OB-fold protein which binds to any target of interest. This composition also generally contains a pharmaceutically or cosmetically acceptable excipient for topical use.

As seen above, said wild-type OB-fold protein also encompasses the OB-fold domains. Preferably, the variant used in the context of the present invention contains a maximum of 150 amino acids, more preferably a maximum of 100 amino acids. In one particular embodiment, it contains a maximum of 70 amino acids.

The number of mutated residues in said variant (relative to the wild-type protein) is comprised between 5 and 32. In other embodiments, these variants preferably have at least 5, more preferably at least 8, even more preferably at least 10, but generally less than 32, more preferably less than 24, even more preferably less than 20 or less than 15 substituted amino acids compared with the wild-type OB-fold protein (or domain). It is preferred when 8, 9, 10, 11, 12 or 13 amino acids are mutated relative to the wild-type protein. These mutated amino acids are located in the site of binding of the OB-fold protein with its natural ligand. They are generally distributed over the whole of this binding domain. Given the structure of this binding domain, certain mutated residues are found in a (generally several, in particular two or three) beta sheet.

In one particular embodiment, these variants can also comprise amino acid insertions in loops linking the beta sheets of the OB-fold. Thus, between 1 and 15 amino acids can be introduced into loop 1 and/or into loop 4 and/or into loop 3 (the loops being numbered in the same way as in WO 2008/068637).

In one particular embodiment, said wild-type OB-fold protein is chosen from Sac7d or Sac7e coming from *Sulfolobus acidocaldarius,* Sso7d coming from *Sulfolobus solfataricus,* DBP 7 coming from *Sulfolobus tokodaii,* Ssh7b coming from *Sulfolobus shibatae,* Ssh7a coming from *Sulfolobus shibatae,* and p7ss coming from *Sulfolobus solfataricus.*

It is therefore the protein with which the variant used in the topical composition of the present invention is compared.

The various sequences of the Sac7d, Sso7d, Sac7e, Ssh7b, Ssh7a, DBP7 and Sis7 proteins are represented by SEQ ID No. 1 to SEQ ID No. 7 respectively.

A variant of a protein of this Sac7d family is called a nanofitin. The invention is thus preferentially implemented on variants of the proteins represented by SEQ ID No. 1 to SEQ ID No. 7, in particular on variants of Sac7d.

The concentration of the variant in the composition according to the present invention is generally greater than 10 ng/ml and less than 600 mg/ml. Indeed, in the case of an ocular application, the concentration of protein does not need to be very high. It is therefore generally less than 10 mg/ml, preferably less than 1 mg/ml, preferably less than 500 ng/ml, or than 250 ng/ml, or even less than 100 ng/ml. Likewise, while the concentration can be as low as 10 ng/ml, it is preferably greater than 50 ng/ml, or even greater than 100 ng/ml.

In the context of a topical use by application to the skin (or to the scalp), the concentration of the product can generally be greater. Thus, the concentration will generally be greater than 10 mg/ml, preferably greater than 50 mg/ml, or preferably greater than 100 mg/ml, even more preferably greater than 200 mg/ml.

The variant present in the composition according to the invention binds specifically to a target of interest. In fact, it has been selected, by means of a method as described in WO 2008/068637 or WO 2007/139397, for its binding specificity with said target of interest. Moreover, the methods described in these patent applications make it possible to obtain affinities of the order of one micromolar (WO 2007/139397) or of one nanomolar (WO 2008/068637).

The targets of interest are chosen according to the disease that it is desired to treat. Mention may thus be made of any antigen, antibody, cell protein, circulating protein, or peptides. It is also possible to target an active ingredient of a medicament, or a particular nucleic acid. It is in particular envisioned that the target of interest is an interleukin, a cytokine, a cytokine or interleukin receptor, a protein encoded by an oncogene, a surface protein of a microorganism, or a microorganism lipopolysaccharide.

In one particular embodiment, the topical composition according to the invention is intended to be applied to the skin.

In another embodiment, this topical composition is intended to be applied at the ocular level.

The form of the topical composition according to the invention is conventional, and depends in particular on the site of administration (skin or eye).

Thus, this composition may be in a liquid form (in particular an eye lotion for an ocular application), pasty form or solid form. It can be in the form of a cream, an ointment, a salve, a powder, a gel, an emulsion (oil-in-water or water-in-oil) or a foam. Water-based formulations optionally containing organic solvents (such as ethanol) are particularly suitable for these compositions.

It can also be in the form of an impregnated pad, a wipe, a spray, an aerosol, a lotion, a stick or a shampoo.

The composition according to the invention can also be in the form of a suspension of microspheres or nanospheres or of lipid or polymeric vesicles or of polymeric patches and hydrogels which allow controlled release of the active ingredients. This composition for topical application can be in anhydrous form, in aqueous form or in the form of an emulsion.

In one particular embodiment, the topical composition according to the invention is in the form of a patch (transdermal system). Such systems can in particular allow controlled release of the active ingredient.

Such a system generally comprises a protective sheet (support layer) which is impermeable to the substance of interest (the variant of the OB-fold protein in the context of the present invention), a reservoir containing the substance of interest, an element controlling the delivery of the substance of interest to the skin, through a (pressure-sensitive) adhesive layer enabling the device to be held in place on the skin, and a protective layer which can be detached before application to the skin. It is possible for the same element to accomplish several functions (for example reservoir, control of release and adhesion). Such devices are known in the prior art.

The variants of the OB-fold proteins, used in the composition according to the invention, can be produced by solid-phase chemical synthesis or by genetic recombination. The chemical synthesis can be carried out, for example, with an Applied Biosystems automatic peptide synthesizer, mod. 433A., or by Fmoc chemistry which uses the fluorenylmethyloxycarbonyl group for temporary protection of the α-amino function of the amino acids.

However, it is preferred to produce the variants that can be used in the context of the invention by genetic engineering, in particular by integrating a nucleic acid sequence encoding said polypeptide into an expression vector. This expression vector is then introduced into a host cell (bacteria such as *Escherichia coli* are particularly suitable), which is cultured under culture conditions allowing the synthesis of the polypeptide (use may in particular be made of inducible promoters upstream of the polypeptide in the expression vector). The polypeptide synthesized is then recovered. Molecules of any type can then be grafted in the N- or C-terminal position of the polypeptide.

Those skilled in the art are aware of the methods for producing polypeptides, which are in particular described in the book by Sambrook, Fritsch and Maniatis, Molecular Cloning, A Laboratory Manual, $2^{nd}$ edition.

The composition according to the invention can contain variants of the OB-fold protein, alone or with other active ingredients. Thus, the composition can also contain at least one agent chosen from antibacterial, antiparasitic, antifungal, anti-inflammatory, antipruritic, anesthetic, antiviral, keratolytic, free-radical-scavenger, antiseborrheic, antidandruff and anti-acne agents and agents for modulating differentiation and/or proliferation and/or pigmentation of the skin.

This composition can also contain a pH regulator, in particular for enabling the pH to be regulated around pH=7.

The variants of the OB-fold protein can also be fused with an active protein, in particular in order to increase their half-life time.

The composition according to the invention can also be used in an in vivo diagnostic method. Thus, in one particular embodiment, the variant of the OB-fold protein is coupled to a detection or contrast agent. This makes it possible in particular to follow this contrast agent and to determine the organs to which the variant of the OB-fold protein binds (thereby indicating the presence of the target of interest).

The invention also relates to a process for preparing a topical composition, comprising the step of mixing a variant of a wild-type OB-fold protein with a pharmaceutically or cosmetically acceptable excipient for topical use.

In one particular embodiment, said composition is intended to be applied to the skin. The excipient thus preferably allows the preparation of a composition which can be spread on the skin, such as an ointment, a salve or a lotion.

In another embodiment, said composition is intended to be applied to the eye, and the excipients are chosen accordingly. Eye lotions and eye drops are thus in particular obtained.

The invention also relates to a topical composition, according to the invention, containing a variant of a wild-type OB-fold protein, said variant having between 5 and 32 mutated residues in the interface of binding of said wild-type OB-fold protein to its natural ligand, as a medicament. In this particular case, said variant binds specifically to a target of interest, which is a therapeutic target.

The invention also relates to a topical composition according to the invention for treating a dermatological or ophthalmological disorder or disease. In this embodiment, the variant of the OB-fold protein used targets (binds to) an etiological factor of the intended disease or a therapeutic target associated with this disease.

In this embodiment, a variant of the OB-fold protein is therefore selected, in particular by means of the screening methods described in WO 2008/068637, said variant binding to a therapeutic target (etiological effector or factor) involved in the disease or the disorder that it is desired to treat, and this variant is formulated in a composition for topical application.

The invention also relates to a cosmetic composition comprising a topical composition according to the invention and to the cosmetic use of a topical composition according to the invention.

The invention also relates to a method for treating a dermatological or ophthalmological disorder or disease, characterized in that a topical composition according to the invention, containing an OB-fold protein targeting, preferably, an etiological factor or a therapeutic target characteristic of said disease or of said disorder, is applied locally (to the skin or at the ocular level as required).

EXAMPLES

In all the examples, nanofitins, as defined above, i.e. variants of Sac7d, obtained by screening a combinatorial library against a target of interest, according to a method similar to the method described in WO 2008/068637, are used. Since the objective of these examples is to demonstrate that the OB-fold proteins, and in particular the nanofitins, are capable of crossing the skin barrier or penetrating into the eye, without this being dependent on the sequence of the protein, the sequences of the nanofitins and the targets of interest are not specified.

Example 1

Test for Penetration of Nanofitins through a Model of Human Skin

The test used is the Franz cell diffusion test.

Franz cells are used to determine, ex vivo, the skin penetration of exogenous substances, and to actually measure the speed of passage through the various layers of the skin barrier of the molecules constituting the active ingredient deposited at the surface of the skin.

A solution containing the molecule to be studied is deposited in a "donor" department of the device. The molecule then diffuses through a membrane (in the case in point the skin) and is collected in a "receiver" compartment.

In practice, after having removed the hypodermal layer (adipose tissue), the skin fragment is deposited on a diffusion cell, called a Franz cell. The deep face of the dermis is in contact with a receiver solution which is supposed to replace the interstitial fluid of the skin. A solution containing the molecule studied is deposited on top of the skin. At regular time intervals, the receiver solution is sampled in order to assay the molecule which has passed through the defatted skin and a new solution then replaces said receiver solution.

The assaying of substances present in the receiver phase sampled makes it possible to determine either the amount of molecules having passed through the skin, or the flow (in nanograms/$cm^2$/hour).

Nanofitins resulting from screenings of a library of Sac7d variants for their affinity against three different targets of interest, involved in skin or ophthalmological diseases, were tested. These nanofitins were produced in a bacterial system and thus bind to different ligands.

Six thawed fragments of human skin (thickness 1 mm), from the same donor, were used.

The receiver compartment was filled with PBS (phosphate buffered saline, pH 7.4; 5.8 ml). The membrane was placed on the receiver medium.

100 μl of each formulation containing 5 mg/ml of nanofitin were deposited on the membrane. The exchange surface area was 2 $cm^2$.

The temperature was maintained at 35° C. throughout the experiment on the receiver side, corresponding to a temperature of 32° C. at the external surface of the human skin.

At each following sampling period: 0 h and 24 h, 500 μl of liquid were removed from the receiver side and replaced with PBS.

On the donor side, at t=24 h, the skin was rinsed with 5 ml of PBS.

At the end of the sampling period, the 2 $cm^2$ of skin were removed from the Franz cell device and placed in an ultrasonic bath in 1 ml of PBS.

The nanofitin concentration was measured on each of the samples taken, using the BioLayer Interferometry technology which makes it possible to measure the interaction between two proteins. In the case in point, the nanofitin content is measured by the recognition of a poly-Histidine tag which is coupled to said nanofitins beforehand.

The results are the following:

The percentage of nanofitins found on the receiver side is spread out, according to the nanofitin, between 8% and 17%. The skin permeability standard used is caffeine, which in the experimental context has a permeability of the order of 10%.

These results show that the nanofitins actually pass through human skin, and that this result is not dependent on the target against which the nanofitin was generated and which it binds.

Example 2

Test for Penetration of Nanofitins through Rabbit Cornea

Three male rabbits (Fauve de Bourgogne) were used.

The principle is the same as for the skin permeability.

Two reaction chambers were used for the study of the permeability of each formulation (NF1, NF2 and NF3).

3 ml of formulation containing each nanofitin were placed on the donor side of the reaction chambers and 3 ml of PBS were placed on the receiver side. Freshly taken corneal tissues were placed between the two half-chambers.

The temperature was maintained at 37° C. throughout the study and the oxygenation was provided by continuous perfusion of carbogen (95% $O_2$, 5% $CO_2$). The exchange surface area was 0.5 $cm^2$.

At each following sampling period: 0 h, 2 h and 4 h, 500 μl of liquid were taken from the receiver side and replaced with PBS.

100 μl of liquid were taken from the donor side and were not replaced.

At the end of the sampling period, the 0.5 $cm^2$ of corneas were removed from the reaction chamber and scraped with a scalpel. 1 ml of PBS was added to the samples, which were homogenized.

The nanofitin concentration was measured on each of the samples taken, using the BioLayer Interferometry technology which makes it possible to measure the interaction between two proteins. In the case in point, the nanofitin content is measured by the recognition of a poly-Histidine tag which is coupled to said nanofitins beforehand.

The results are the following:

The amount of nanofitins found on the receiver side makes it possible to calculate an apparent permeability (cm/s) of, according to the nanofitins, between $5\times10^{-6}$ and $2\times10^{-6}$. In comparison with the standards used in this type of experimental protocol, the nanofitins tested exhibit a permeability comparable to that of norfloxacin ($1.1\times10^{-}$in this experimental model), which is a molecule that exhibits good penetration of the cornea and that is used in ophthalmology in an eye lotion for local antibacterial treatment of severe ocular infections caused by norfloxacin-sensitive microorganisms.

These results show that the nanofitins actually cross the cornea, and that this result is not dependent on the target against which the nanofitin was screened.

Example 3

Evaluation of the Skin Permeability of the Nanofitins In Vivo

Purpose: In order to verify the skin penetration of nanofitins and the preservation of their properties, in particular their property of neutralizing the receptor-ligand relationship, inflammation models of psoriasis type were used and the reduction in inflammation (PASI score) after topical administration of anti-inflammatory nanofitins directly to the skin was measured.

These nanofitins target two different cytokines involved in psoriasiform inflammation, but with different localizations, from the basal layers of the dermis just into the epidermis (Nestle et al., Nature Reviews Immunology 9, 679-691, 2009). The nanofitins in question neutralize the binding of the targeted cytokines with their receptor. In order to inhibit the action of these cytokines during inflammation of psoriasis type, it is necessary to reach the layers where they are located, either systemically as therapeutic antibodies do, or topically via the skin. The measurement of an anti-inflammatory effect by topical administration of nanofitins thus attests to penetration of the nanofitins through the skin and to an associated therapeutic efficacy.

Method:

The local application of imiquimod (Aldara) to the internal face of the ears of mice causes a skin inflammation similar to psoriasis (Van der Fits et al., J Immunol. 2009 May 1; 182(9):5836-45, Flutter et al., Eur J Immunol. 2013 December; 43(12):3138-46). This protocol was applied on Balb/c mice 6-8 weeks old, on both ears.

Four groups of mice were used.

A control group, in which the mice did not receive imiquimod (negative control).

Three experimental groups, in which the mice received imiquimod on both ears, and also a treatment on the right ear. These three experimental groups are:

A nanofitin efficacy test group: four different nanofitins were applied to the right ear of the mice (n=4) for each experimental subgroup of this group. The nanofitins were formulated in PBS with optionally 20% EtOH.

A control group in which the mice received the nanofitin carrier alone (PBS, 20% EtOH) on the treated ear.

A control group in which the mice received a control treatment (clobetazole) topically as treatment positive control.

The protocol was organized as follows:

Daily administration of imiquimod for seven consecutive days, one admin/day in the morning.

Administration of the nanofitins or of the other controls starting from the third day up to the seventh day, one admin/day in the evening.

Observation and determination of the PAST score from day 4 to day 7, in the morning before administration of the imiquimod.

Sacrifice on the eighth day after determination of the PASI score.

The measurement of the efficacy consisted of the observation by two operators, independently and blind, of the parameters of the PASI score for each ear: thickness, desquamation, redness on a grade of 0 (lowest) to 4 (highest). A total score is obtained by adding the various scores for each ear of each animal.

The four nanofitins target cytokines involved in the inflammatory phenotype caused by imiquimod and prevent said cytokines from binding to their respective receptors, as was previously verified in vitro (BioLayer Interferometry). They were administered at 10 mg/kg (with the exception of the second at 20 mg/kg) in a solution of PBS/20% EtOH or PBS without ethanol.

Results: For all the nanofitins applied, a very significant reduction in the inflammation on the treated ear was noted in comparison with the nontreated ear (FIG. 1).

The inflammation of the nontreated ears was maintained whatever the group, with the exception of the group having received clobetazole.

The clobetazole was administrated as a cream and the mice of this group licked their ears thoroughly in this group only. A reduction in the inflammation on the nontreated left ear is also observed in this group. A systemic effect after ingestion is thus therefore very probable with an effect on both ears.

Conclusion: The topical administration of anti-inflammatory nanofitins made it possible to induce a reduction of more than 30%, and possibly exceeding 80%, in the inflammatory manifestations after five days of treatment.

These scores attest to a very significant in vivo efficacy of the nanofitins used, and demonstrate their ability to naturally cross cell barriers in neutral formulations, while at the same time retaining a neutralizing activity. The nanofitins can thus be used as treatments which are both targeted and topical for the treatment of pathological conditions of which the targets or effectors are under the skin.

---

The invention claimed is:

1. A method for administering a variant of a wild-type OB-fold protein, the method comprising topically applying a dermatological composition comprising said variant on skin of a patient, wherein said variant passes through the skin of the patient, and wherein said variant has between 5 and 20 mutated residues in the interface of binding of said wild-type OB-fold protein to its natural ligand, wherein said wild-type OB-fold protein is selected from the group consisting of Sac7d or Sac7e derived from *Sulfolobus acidocaldarius*, Sso7d derived from *Sulfolobus solfataricus*, DBP 7 derived from *Sulfolobus tokodaii*, Ssh7b derived from *Sulfolobus shibatae*, Ssh7a derived from *Sulfolobus shibatae*, and p7ss derived from *Sulfolobus solfataricus*, and wherein said mutated residues are selected from the group consisting of V2, K3, K5, K7, Y8, K9, G10, E14, T17, K21, K22, W24, V26, G27, K28, M29, S31, T33, D36, N37, G38, K39, T40, R42, A44, S46, E47, K48, D49, A50 and P51 of Sac7d.

2. The method of claim 1, wherein the dermatological composition comprises between 10 mg/ml and 600 mg/ml of said variant.

3. The method of claim 1, wherein said variant binds to a target selected from the group consisting of an antigen, an antibody, a cell protein, a circulating protein, a peptide, an active ingredient of a medicament, and a nucleic acid.

4. The method of claim 1, wherein the dermatological composition is in the form of an aqueous, oily or aqueous-alcoholic solution, an emulsion, a microemulsion, an aqueous gel, an anhydrous gel, a serum, a dispersion of vesicles, a lotion, a gel, a cream, a foam, an aerosol or a spray.

5. The method of claim 1, wherein the dermatological composition comprises at least one agent selected from the group consisting of an antibacterial, an antiparasitic, an antifungal, an anti-inflammatory, antipruritic, an anesthetic, an antiviral, a keratolytic, a free-radical-scavenger, an anti-seborrheic, an antidandruff, an anti-acne agent, and an agent for modulating the differentiation and/or proliferation and/or pigmentation of the skin.

6. The method of claim 1, wherein at least 8% of said variant in the dermatological composition passes through human skin according to the Franz cell diffusion test.

7. The method of claim 1, wherein said variant has between 5 and 15 mutated residues in the interface of binding of said wild-type OB-fold protein to its natural ligand.

8. The method of claim 1, wherein the number of mutated residues in the interface of binding of said wild-type OB-fold protein to its natural ligand is selected from the group consisting of 8, 9, 10, 11, 12 and 13.

9. A method for having a protein penetrate through the skin of a patient, the method comprising topically applying a dermatological composition comprising said variant on skin of the patient, wherein said variant passes through the skin of the patient, and wherein said variant has between 5 and 20 mutated residues in the interface of binding of said wild-type OB-fold protein to its natural ligand, wherein said wild-type OB-fold protein is selected from the group consisting of Sac7d or Sac7e derived from *Sulfolobus acidocaldarius*, Sso7d derived from *Sulfolobus solfataricus*, DBP 7 derived from *Sulfolobus tokodaii*, Ssh7b derived from *Sulfolobus shibatae*, Ssh7a derived from *Sulfolobus shibatae*, and p7ss derived from *Sulfolobus solfataricus*, and wherein said mutated residues are selected from the group consisting of V2, K3, K5, K7, Y8, K9, G10, E14, T17, K21, K22, W24, V26, G27, K28, M29, S31, T33, D36, N37, G38, K39, T40, R42, A44, S46, E47, K48, D49, A50 and P51 Sac7d.

10. The method of claim 9, wherein at least 8% of the variant in the dermatological composition passes through human skin according

SEQUENCE LISTING

```
<160> NUMBER OF SEQ ID NOS: 8

<210> SEQ ID NO 1
<211> LENGTH: 66
<212> TYPE: PRT
<213> ORGANISM: Sulfolobus acidocaldarius

<400> SEQUENCE: 1

Met Val Lys Val Lys Phe Lys Tyr Lys Gly Glu Glu Lys Glu Val Asp
1               5                   10                  15

Thr Ser Lys Ile Lys Lys Val Trp Arg Val Gly Lys Met Val Ser Phe
            20                  25                  30

Thr Tyr Asp Asp Asn Gly Lys Thr Gly Arg Gly Ala Val Ser Glu Lys
        35                  40                  45

Asp Ala Pro Lys Glu Leu Leu Asp Met Leu Ala Arg Ala Glu Arg Glu
    50                  55                  60

Lys Lys
65
```

```
<210> SEQ ID NO 2
<211> LENGTH: 64
<212> TYPE: PRT
<213> ORGANISM: Sulfolobus solfataricus

<400> SEQUENCE: 2

Met Ala Thr Val Lys Phe Lys Tyr Lys Gly Glu Glu Lys Glu Val Asp
1               5                   10                  15

Ile Ser Lys Ile Lys Lys Val Trp Arg Val Gly Lys Met Ile Ser Phe
            20                  25                  30

Thr Tyr Asp Glu Gly Gly Gly Lys Thr Gly Arg Gly Ala Val Ser Glu
        35                  40                  45

Lys Asp Ala Pro Lys Glu Leu Leu Gln Met Leu Glu Lys Gln Lys Lys
    50                  55                  60

<210> SEQ ID NO 3
<211> LENGTH: 65
<212> TYPE: PRT
<213> ORGANISM: Sulfolobus acidocaldarius

<400> SEQUENCE: 3

Met Ala Lys Val Arg Phe Lys Tyr Lys Gly Glu Glu Lys Glu Val Asp
1               5                   10                  15

Thr Ser Lys Ile Lys Lys Val Trp Arg Val Gly Lys Met Val Ser Phe
            20                  25                  30

Thr Tyr Asp Asp Asn Gly Lys Thr Gly Arg Gly Ala Val Ser Glu Lys
        35                  40                  45

Asp Ala Pro Lys Glu Leu Met Asp Met Leu Ala Arg Ala Glu Lys Lys
    50                  55                  60

Lys
65

<210> SEQ ID NO 4
<211> LENGTH: 64
<212> TYPE: PRT
<213> ORGANISM: Sulfolobus shibatae

<400> SEQUENCE: 4

Met Val Thr Val Lys Phe Lys Tyr Lys Gly Glu Glu Lys Glu Val Asp
1               5                   10                  15

Thr Ser Lys Ile Lys Lys Val Trp Arg Val Gly Lys Met Ile Ser Phe
            20                  25                  30

Thr Tyr Asp Glu Gly Gly Gly Lys Thr Gly Arg Gly Ala Val Ser Glu
        35                  40                  45

Lys Asp Ala Pro Lys Glu Leu Leu Gln Met Leu Glu Lys Gln Lys Lys
    50                  55                  60

<210> SEQ ID NO 5
<211> LENGTH: 64
<212> TYPE: PRT
<213> ORGANISM: Sulfolobus shibatae

<400> SEQUENCE: 5

Met Ala Thr Val Lys Phe Lys Tyr Lys Gly Glu Glu Lys Gln Val Asp
1               5                   10                  15

Ile Ser Lys Ile Lys Lys Val Trp Arg Val Gly Lys Met Ile Ser Phe
            20                  25                  30
```

Thr Tyr Asp Glu Gly Gly Gly Lys Thr Gly Arg Gly Ala Val Ser Glu
        35                  40                  45

Lys Asp Ala Pro Lys Glu Leu Leu Gln Met Leu Glu Lys Gln Lys Lys
 50                  55                  60

<210> SEQ ID NO 6
<211> LENGTH: 64
<212> TYPE: PRT
<213> ORGANISM: Sulfolobus sp.

<400> SEQUENCE: 6

Met Val Thr Val Lys Phe Lys Tyr Lys Gly Glu Glu Lys Glu Val Asp
 1               5                  10                  15

Ile Ser Lys Ile Lys Lys Val Trp Arg Val Gly Lys Met Ile Ser Phe
            20                  25                  30

Thr Tyr Asp Asp Asn Gly Lys Thr Gly Arg Gly Ala Val Ser Glu Lys
        35                  40                  45

Asp Ala Pro Lys Glu Leu Leu Gln Met Leu Glu Lys Ser Gly Lys Lys
 50                  55                  60

<210> SEQ ID NO 7
<211> LENGTH: 64
<212> TYPE: PRT
<213> ORGANISM: Sulfolobus islandicus

<400> SEQUENCE: 7

Met Val Thr Val Lys Phe Lys Tyr Lys Gly Glu Glu Lys Gln Val Asp
 1               5                  10                  15

Thr Ser Lys Ile Lys Lys Val Trp Arg Val Gly Lys Met Ile Ser Phe
            20                  25                  30

Thr Tyr Asp Glu Gly Gly Gly Lys Thr Gly Arg Gly Ala Val Ser Glu
        35                  40                  45

Lys Asp Ala Pro Lys Glu Leu Leu Gln Met Leu Glu Lys Gln Lys Lys
 50                  55                  60

<210> SEQ ID NO 8
<211> LENGTH: 67
<212> TYPE: PRT
<213> ORGANISM: Artificial
<220> FEATURE:
<223> OTHER INFORMATION: Synthetic consensus sequence
<220> FEATURE:
<221> NAME/KEY: VARIANT
<222> LOCATION: (2)..(2)
<223> OTHER INFORMATION: Xaa is V, A or T
<220> FEATURE:
<221> NAME/KEY: VARIANT
<222> LOCATION: (3)..(3)
<223> OTHER INFORMATION: Xaa is T or K
<220> FEATURE:
<221> NAME/KEY: VARIANT
<222> LOCATION: (5)..(5)
<223> OTHER INFORMATION: Xaa is R or K
<220> FEATURE:
<221> NAME/KEY: VARIANT
<222> LOCATION: (14)..(14)
<223> OTHER INFORMATION: Xaa is E or Q
<220> FEATURE:
<221> NAME/KEY: VARIANT
<222> LOCATION: (17)..(17)
<223> OTHER INFORMATION: Xaa is T or I
<220> FEATURE:
<221> NAME/KEY: VARIANT
<222> LOCATION: (30)..(30)
<223> OTHER INFORMATION: Xaa is A, V or I

```
<220> FEATURE:
<221> NAME/KEY: VARIANT
<222> LOCATION: (36)..(38)
<223> OTHER INFORMATION: Xaa Xaa Xaa is EGG or DN-, wherein a -
      indicates the amino acid at that position is absent.
<220> FEATURE:
<221> NAME/KEY: VARIANT
<222> LOCATION: (56)..(56)
<223> OTHER INFORMATION: Xaa is M or L
<220> FEATURE:
<221> NAME/KEY: VARIANT
<222> LOCATION: (57)..(57)
<223> OTHER INFORMATION: Xaa is Q or D
<220> FEATURE:
<221> NAME/KEY: VARIANT
<222> LOCATION: (60)..(67)
<223> OTHER INFORMATION: Xaa Xaa Xaa Xaa Xaa Xaa Xaa Xaa represents
      A-------, ARAE----, EKQKK---, EKSGKK--, ARAEREKK, ARAEKKK-,
      ACAEREKK or ACAEKKK-, wherein a - indicates the amino acid at that
      position is absent.

<400> SEQUENCE: 8

Met Xaa Xaa Val Xaa Phe Lys Tyr Lys Gly Glu Glu Lys Xaa Val Asp
1               5                   10                  15

Xaa Ser Lys Ile Lys Lys Val Trp Arg Val Gly Lys Met Xaa Ser Phe
            20                  25                  30

Thr Tyr Asp Xaa Xaa Xaa Gly Lys Thr Gly Arg Gly Ala Val Ser Glu
        35                  40                  45

Lys Asp Ala Pro Lys Glu Leu Xaa Xaa Met Leu Xaa Xaa Xaa Xaa Xaa
    50                  55                  60

Xaa Xaa Xaa
65
```